United States Patent

Nakada et al.

[11] Patent Number: 6,018,084
[45] Date of Patent: Jan. 25, 2000

[54] PROCESS FOR PRODUCING 1,1,1,3,3-PENTAFLUOROPROPANE

[75] Inventors: Tatsuo Nakada; Hirokazu Aoyama; Akinori Yamamoto, all of Settsu, Japan

[73] Assignee: Daikin Industries Ltd., Osaka, Japan

[21] Appl. No.: 09/091,820

[22] PCT Filed: Oct. 8, 1996

[86] PCT No.: PCT/JP96/02942

§ 371 Date: Jun. 25, 1998

§ 102(e) Date: Jun. 25, 1998

[87] PCT Pub. No.: WO97/24307

PCT Pub. Date: Jul. 10, 1997

[30] Foreign Application Priority Data

Dec. 29, 1995 [JP] Japan ..................... 7-354118

[51] Int. Cl.$^7$ ............................................. C07C 17/08
[52] U.S. Cl. .................... 570/166; 570/167; 570/168; 570/169
[58] Field of Search ..................... 570/166, 167, 570/168, 169

[56] References Cited

U.S. PATENT DOCUMENTS 5,710,352  1/1998  Tung ........................................ 570/166

*Primary Examiner*—Elli Peselev
*Attorney, Agent, or Firm*—Armstrong, Westerman, Hattori, McLeland & Naughton

[57] ABSTRACT

A manufacturing method for 1,1,1,3,3-pentafluoropropane comprises a first process, in which 1,1,1-trifluoro-3-chloro-2-propene is obtained by inducing a reaction between 1,1,1,3,3-pentafluoropropane and hydrogen fluoride in the vapor phase, and a second process, in which the 1,1,1,3,3-pentafluoropropane is obtained by inducing a reaction between 1,1,1-trifluoro-3-chloro-2-propene and hydrogen in the vapor phase, and 1,1,1-trifluoro-3-chloro-2-propene obtained in the first process is supplied to the second process after removing the HCl by-products. This invention can provide a new economic manufacturing method of 1,1,1,3,3-pentafluoropropane with high yield and selectivity.

2 Claims, 1 Drawing Sheet

PROCESS FOR PRODUCING 1,1,1,3,3-PENTAFLUOROPROPANE

INDUSTRIAL FIELDS WHERE THE INVENTION CAN BE UTILIZED

This invention relates to a method to produce 1,1,1,3,3-pentafluoropropane, which does not destroy the ozone layer and is important for industrial fields as HFC blowing agents, refregerants and propellants.

PRIOR ART

Because of these advantages, a method to produce 1,1,1,3,3-pentafluoropropane is urgently needed to be established.

The known methods of producing 1,1,1,3,3-pentafluoropropane are as follows. Carbon tetrachloride and vinylidene chloride are prepared and an addition reaction is triggered. The reaction product, 1,1,1,3,3,3-hexachloropropane, is fluorinated to produce 1,1,1,3,3-pentafluoro-3-chloropropane which is reduced with hydrogen to produce 1,1,1,3,3-pentafluoropropane (WO 95/04022).

Either 1,1,1,3,3-pentafluoro-2,3-dichloropropane or 1,1,1,3,3-pentafluoro-2,2,3-trichloropropane is reduced with hydrogen to produce 1,1,1,3,3-pentafluoropropane (EP 061174).

These well-known methods, however, present technical and cost problems because of the prolonged chemical processes including the process in which the chloride is fluorinated to produce a precursor, and the process in which the obtained compound is reduced with hydrogen.

OBJECT OF THE INVENTION

The object of this invention is to provide a new cost-efficient method to produce 1,1,1,3,3-pentafluoropropane that gives high yield and selectivity without the disadvantages that are common with conventional production techniques.

CONSTRUCTION OF THE INVENTION

In order to solve these problems, a production method for 1,1,1,3,3-pentafluoropropane was thoroughly investigated. As a result, the inventors found that when pentachloropropane is used as a starting material and this is reacted with hydrogen fluoride in the vapor phase, an important point is that an equilibrium exists between the reaction intermediates, 1,1,1-trifluoro-3-chloro-2-propene and 1,1,1,3-tetrafluoro-2-propene, and that when 1,1,1,3,3-pentachloropropane is fluorinated in the vapor phase, 1,1,1-trifluoro-3-chloro-2-propene is obtained and the by-product, hydrogen chloride, is removed and 1,1,1-trifluoro-3-chloro-2-propene is further fluorinated to produce 1,1,1,3,3-pentafluoropropane effectively. As a result of this experiment,1,1,1,3,3-pentafluoropropane is produce with high yield from 1,1,1,3,3-pentachloropropane simply through the process of fluorination. This gives a cost-effective method to produce 1,1,1,3,3-pentafluoropropane to complete this invention.

This invention provides a manufacturing method for 1,1,1,3,3-pentafluoropropane comprising the following two processes: a first process to obtain a mixture, which contains mainly 1,1,1-trifluoro-3-chloro-2-propene, by inducing the reaction between 1,1,1,3,3-pentachloropropane and hydrogen fluoride in gaseous (vapor) phase, and a second process to remove the by-product, hydrogen chloride, from the mixture obtained in the first process, containing mainly 1,1,1-trifluoro-3-chloro-2-propene, and to obtain 1,1,1,3,3-pentafluoropropane by inducing a reaction between the remaining mixture and hydrogen fluoride in gaseous (vapor) phase. According to the claimed manufacturing method, the chemical reaction is triggered in the following two stages.

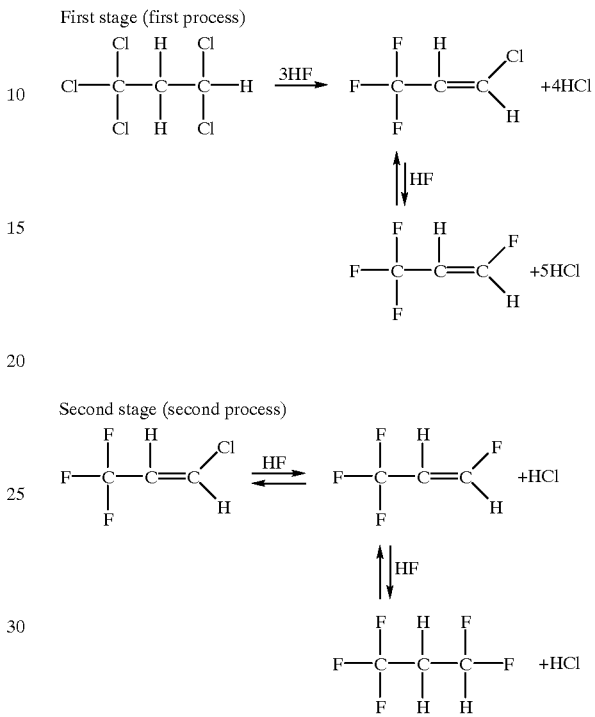

In the first stage (first process) in which 1,1,1,3,3-pentachloropropane is fluorinated with hydrogen fluoride in the vapor phase, there exists an equilibrium between 1,1,1-trifluoro-3-chloro-2-propene and 1,1,1,3-tetrafluoro-2-propene. Because the by-product of HCl promotes a strong tendency towards 1,1,1-trifluoro-3-chloro-2-propene, the main product is 1,1,1-trifluoro-3-chloro-2-propene even if excessive amounts of hydrogen fluoride are used. Although the intermediate, 1,1,1,3-tetrafluoropropene, and the target substance, 1,1,1,3,3-pentafluoropropane, can be obtained through these reactions, their amount is slight.

However, in this invention, after removing the by-product of HCl, the reaction product which mainly contains 1,1,1-trifluoro-3-chloro-2-propene is fluorinated with hydrogen fluoride in the vapor phase in the second stage (second process). Consequently the target substance, 1,1,1,3,3-pentafluoropropane, can be obtained with high yield and selectivity. In the first stage, 1,1,1-trifluoro-3-chloro-2-propene produced in the first stage is useful for an intermediate of medical drugs and agricultural chemicals for introducing a trifluoropropyl group into organic compounds.

EMBODIMENTS OF THE INVENTION

The claimed manufacturing method is explained in detail.

In the first stage described above, 1,1,1,3,3-pentachloropropane and hydrogen fluoride are added in a first reactor which is filled with a fluorinating catalyst to induce the reaction. In order to proceed the reaction, the molar ratio of hydrogen fluoride to the former should be more than three times that of 1,1,1,3,3-pentachloropropane. Adding excessive hydrogen fluoride is recommended to complete the reaction as well as it has no problem so as not to adversely affect the performance of the reactor. If the added excessive hydrogen fluoride is not sufficient, the remaining compound contains too much chlorine. Therefore the molar ratio of the hydrogen fluoride is generally set at a level ranging from five to 20 times that of the 1,1,1,3,3-pentachloropropane.

A third stage follows the first and second stages (first and second processes) described in the above. The mixed gas which mainly contains 1,1,1,3,3-pentafluoropropane is obtained in the second stage. This gas contains 1,1,1,3-tetrafluoro-2-propene and 1,1,1-trifluoro-3-chloro-2-propene. After the separation of 1,1,1,3,3-pentafluoropropane, these two substances are recycled to the second process (the third process).

Because there exists an equilibrium between 1,1,1,3,3-pentafluoropropane and 1,1,1,3-tetrafluoro-2-propene, the third process described above is necessary to obtain 1,1,1,3,3-pentafluoropropane efficiently.

The following reaction formulae demonstrate these processes.

First stage (first process)

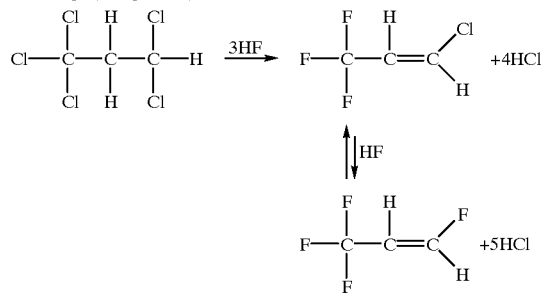

Second stage (second process)

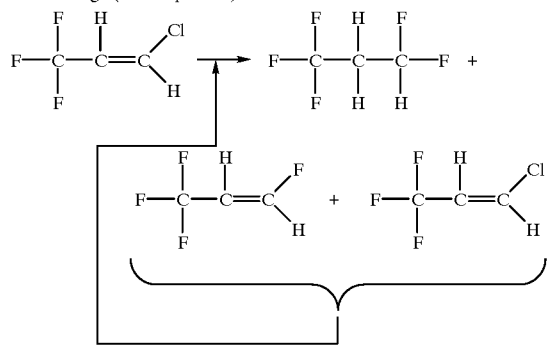

Actually, the gas obtained in the second stage contains 1,1,1-trifluoro-3-chloro-2-propene, 1,1,1,3-tetrafluoro-2-propene, 1,1,1,3,3,-pentafluoropropane, HCl, and excessively added hydrogen fluoride. After removal of the target substance, 1,1,1,3,3-pentafluoropropane and HCl from this mixture, the residual should be introduced into a second reactor.

The HCl, which has a lower boiling point than the other products, can be easily removed by distillation. Other techniques can also be used to remove the HCl besides distillation. Although the obtained gas can be washed with water to remove HCl, hydrogen fluoride is simultaneously removed. In this case, the removed hydrogen fluoride should be recovered.

When the mixture consisting of 1,1,1-trifluoro-3-chloro-2-propene and 1,1,1,3-tetrafluoropropene and hydrogen fluoride is introduced into the second reactor, the molar ratio of the hydrogen fluoride should exceed that of the mixture so that the equilibrium between the 1,1,1,3-tetrafluoro-2-propene and the 1,1,1,3,3-pentafluoropropane leans towards the target substance.

In this case, extra hydrogen fluoride added in the first reactor can be used directly. Additional hydrogen fluoride clan be added as necessary. The molar ratio of the hydrogen fluoride is generally set at a level ranging from five to 20 times t hat of the mixture.

The gas obtained in the second reactor contains the target substance, 1,1,1,3,3-pentafluoro propane, 1,1,1,3-tetrafluoro-2-propene, and 1,1,1-trifluoro-3-chloro-2-propene. These substances can be easily separated by distillation. Ideally, 1,1,1,3-tetrafluoro-2-propene and 1,1,1-trifluoro-3-chloro-2-propene should be reintroduced into the second reactor.

In the processes described above, any type of fluorination catalyst can be used and t he method used to produce the catalyst is not particularly restricted. Fluorination catalysts include chromium fluoride oxide, alumina fluoride. and substances such as fluorinated alumina which carry at least one of the following elements: Cr, Zn, Ti, V, Zr, Mo, Ge, Sn and Pb. Chromium fluoride oxide is prepared by the following treatment. The hydrates of chromium hydroxide (III) and chromium trifluoride (III) are treated with heat and the obtained substances are fluorinated with hydrogen fluoride to produce chromium fluoride oxide. Alumina fluoride is produced by fluorinating alumina with hydrogen fluoride.

Although no specified reaction temperature is necessary, the reaction temperature should be adjusted to the temperature range 100 to 400° C. The optimum temperature ranges from 200 to 300° C. It is difficult to promote the reaction at, temperatures below 100° C. If the reaction temperature exceeds 400° C., the selectivity may decline because of the increase in by-products. The temperatures of the first reactor and that of the second reactor should be adjusted to appropriate levels and they need not necessarily be set to the same temperature.

If the reaction temperature is extremely low, large-scale equipment is necessary to produce an objective amount of the target substance. Extremely high reaction temperature is not preferable because the equilibrium between the 1,1,1,3,3-pentafluoropropane and the 1,1,1,3-tetrafluoro-2-propene leans towards the 1,1,1,3-tetrafluoro-2-propene.

Although there is no restriction on the reaction pressure, the optimum reaction pressure ranges from atmospheric pressure to 20 kg/cm2.

Any type of reaction equipment can be used in this process. Because this invention is based on the catalytic reaction between a gas and a solid, the equipment generally used is either a multipipe fixed bed reactor or a fluidized bed reactor. A movable bed reactor etc. are also suitable. Different types of reactor can be used as the first and second reactors.

FIG. 1 shows a plant which can be used for performing the claimed method.

The raw material used in the claimed production method is 1,1,1,3,3-pentachloropropane which is easily obtained by an addition reaction between carbon tetrachloride and vinyl chloride (Journal of Molecular Catalysis, Vol. 77.51, 1992; Magazine of Industrial Chemistry, Vol. 72, No.7, 1526, 1969).

INDUSTRIAL AVAILABILITY OF THE INVENTION

The claimed manufacturing method comprises the following two processes. In the first process, 1,1,1,3,3- pentachloropropane and hydrogen fluoride are reacted in gaseous (vapor) phase to obtain 1,1,1-trifluoro-3-chloro-2-propene. In the second process, the 1,1,1-trifluoro-3-chloro-2-propene and hydrogen fluoride are reacted in gaseous (vapor)phase to produce 1,1,1,3,3-pentafluoropropane. The gas obtained in the first process, which mainly contains 1,1,1-trifluoro-3-chloro-2-propene, is supplied to the second process after removing the by-product, HCl. This technique is effective for the production of 1,1,1,3,3-pentafluoropropane with high selectivity. Consequently 1,1,1,3,3-pentafluoropropane can be produced from 1,1,1,3,3-pentachloropropane economically and effectively simply through the fluorination process.

The claimed method is adopted to produce a substance: 1,1,1,3,3-pentafluoropropane that does not destroy the ozone layer and that is important for industrial use as HFC blowing agents, refrigerants and propellants. In the first process, 1,1,1-trifluoro-3-chloro-2-propene is produced. This substance is useful for an intermediate of medical drugs and agricultural chemicals for introducing the trifluoropropyl group into organic compounds.

EXAMPLES

Figure 1:
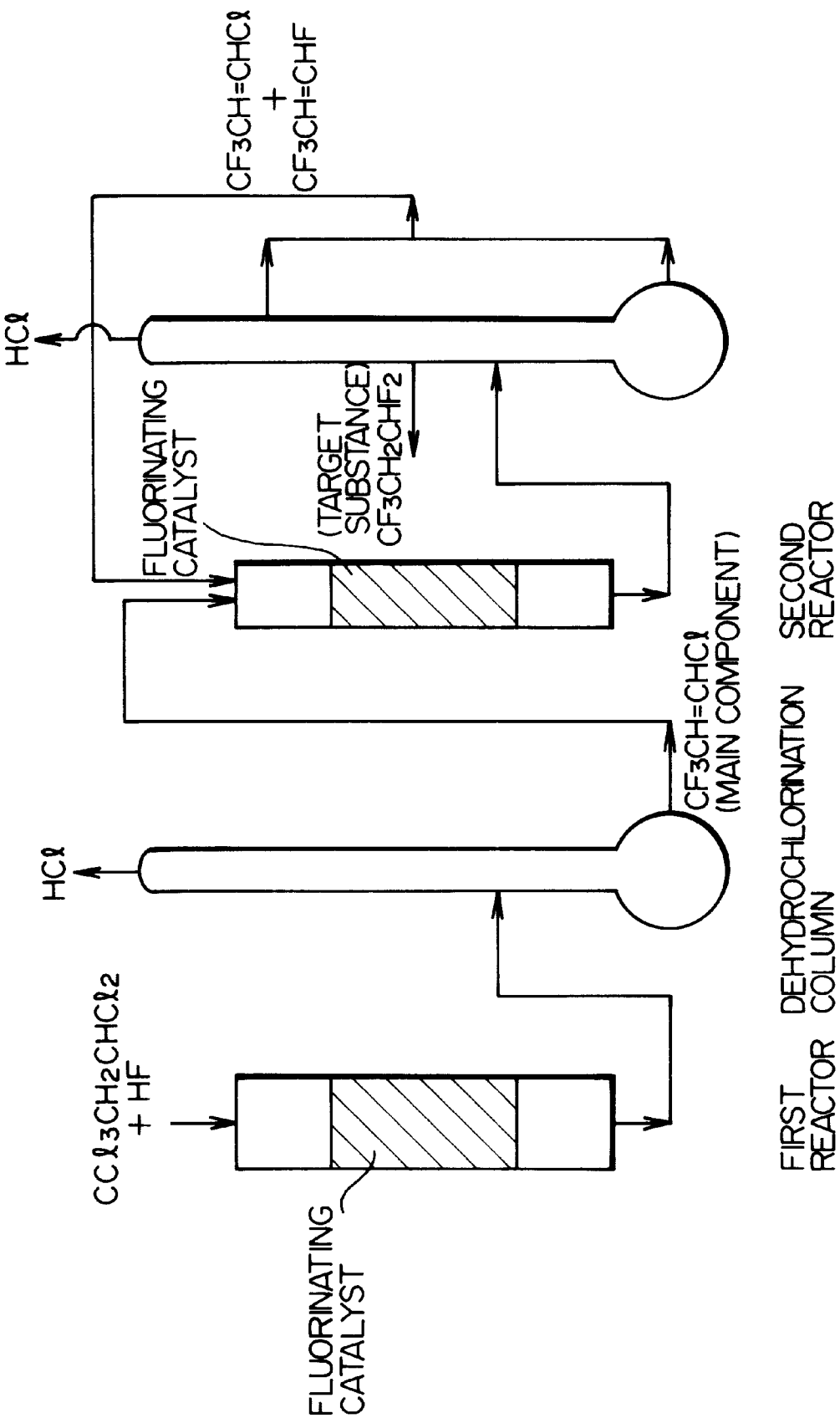
FIG. 1 gives a schematic flow of an example of the equipment used for performing the production method of the present invention.

The present invention will be explained in the following examples.

Example 1

A first reactor:

An aqueous solution of chromium nitrate and an aqueous ammonia were mixed to form a precipitate of chromium hydroxide. A fluorination catalyst was obtained by heat treating the chromium hydroxide. The catalyst was fluorinated by a pretreatment with only hydrogen fluoride passing therethrough before the reaction. A Hastelloy C reaction tube (internal diameter: 20 mm, length: 700 mm) was filled with 20 g of the catalyst and the temperature was increased at 250° C. in a nitrogen stream.

After the nitrogen stream was terminated, 1,1,1,3,3-pentachloropropane and hydrogen fluoride were introduced at flow rates of 20 cc/min and 200 cc/min respectively. The obtained gas was washed with water and dried and then the composition of the produced gas was analyzed by gas chromatography. A mixed gas of the following composition was obtained:

| | |
|---|---|
| 1,1,1,3-tetrafluoro-2-propene | 2.1% |
| 1,1,1,3,3-pentafluoropropane | 5.0% |
| 1,1,1-trifluoro-3-chloro-2-propene | 92.9% |

A second reactor:

The gas obtained in the first reactor was washed with water to remove hydrogen chloride (HCl). After drying, the reaction mixture, which mainly contained 1,1,1-trifluoro-3-chloropropene, was added in a second reactor at flow rate of 20 cc/min accompanied with 200 cc/min of hydrogen fluoride. Conditions in the second reactor were adjusted to match those in the first reactor and a further reaction was induced.

The obtained gas was washed with water and the composition was analyzed by gas chromatography. The mixed gas of the following composition was obtained:

| | |
|---|---|
| 1,1,1,3-tetrafluoro-2-propene | 23.4% |
| 1,1,1,3,3-pentafluoropropane | 52.3% |
| 1,1,1-trifluoro-3-chloro-2-propene | 24.3% |

As demonstrated in this example, the target substance, 1,1,1,3,3-pentafluoropropane, was economically produced with high selectivity simply through the process of fluorination, using 1,1,1,3,3-pentachloropropane as the raw material.

Example 2

The reaction process adopted in this example was the same as that adopted in Example 1 except for the use of fluorinated alumina as the catalyst. The gas obtained in the second reactor was washed with water and its composition was analyzed by gas chromatography and a mixed gas of the following composition was obtained:

| | |
|---|---|
| 1,1,1,3-tetrafluoro-2-propene | 22.9% |
| 1,1,1,3,3-pentafluoropropane | 51.8% |
| 1,1,1-trifluoro-3-chloro-2-propene | 25.3% |

As demonstrated also in this example,the target substance, 1,1,1,3,3-pentafluoropropane, was economically produced with high sellectivity simply through the process of fluorination, using 1,1,1,3,3-pentachloropropane as the raw material.

Example 3

As shown in Example 1, the first reactor was filled with a catalyst. An SUS made distiller (second reactor) was attached to the outlet of the first reactor so that the obtained gas could be rectified. In this system, 1,1,1-trifluoro-3-chloropropene and hydrogen fluoride were introduced at rates of 20 cc/min and 200 cc/min respectively. The products were introduced into the distillation column. In addition to the 1,1,1,3-tetrafluoropropene with low boiling point and unreacted 1,1,1-trifluoro-3-chloropropene with high boiling point, extra hydrogen fluoride was introduced into the distillation column for recycling.

As the reaction in the distillation column stabilized, the introduction amount of hydrogen fluoride was gradually decreased until the whole of the reaction system was stabilized. When the system was stable, the gas sample was collected from the outlet of the second reactor. The collected sample was washed with water and analyzed by gas chromatography and a mixed gas of the following composition was found to be obtained:

| | |
|---|---|
| 1,1,1,3-tetrafluoropropene | 28.6% |
| 1,1,1,3,3-pentafluoropropane | 61.3% |
| 1,1,1-trifluoro-3-chloro-2-propene | 10.1% |

The gas obtained from the middle outlet of the distillation column was washed with water and analyzed by gas chromatography and a mixed gas of the following composition was obtained:

| | |
|---|---|
| 1,1,1,3-tetrafluoropropene | 1.6% |
| 1,1,1,3,3-pentafluoropropane | 98.4% |

After collecting the gas produced during a specified period of time, the recovery rate was 97%.

As demonstrated in this example, the target substance, 1,1,1,3,3-pentafluoropropane, was economically produced with high selectivity, although the substances in the second reactor were recycled.

What is claimed is:

1. A manufacturing method of 1,1,1,3,3-pentafluoropropane comprising a first process in which 1,1,1-trifluoro-3-chloro-2-propene is mainly obtained by a reaction of 1,1,1,3,3-pentachloropropane and hydrogen fluoride in gaseous phase and in the presence of a fluorinating catalysts, and a second process in which 1,1,1,3,3-pentafluoropropane is obtained by a reaction of hydrogen fluoride and the gas obtained in the first process from which hydrogen chloride has been removed in gaseous phase and in the presence of a fluorinating catalyst.

2. A manufacturing method as defined by claim 1 having a third process in which 1,1,1,3,3-pentafluoropropane is recovered and hydrogen chloride is removed from the gas collected in the second process, and the residual gas mainly containing 1,1,1,3-tetrafluoro-2-propene and 1,1,1-trifluoro-3-chloro-2-propene is recycled to a second process.

* * * * *